US012023042B2

(12) United States Patent
Sugimoto et al.

(10) Patent No.: US 12,023,042 B2
(45) Date of Patent: Jul. 2, 2024

(54) SURGICAL INSTRUMENT (71) Applicant: KYOCERA Corporation, Kyoto (JP)

(72) Inventors: Kazutaka Sugimoto, Hikone (JP);
Masahiko Hashida, Toyonaka (JP)

(73) Assignee: Kyocera Corporation, Kyoto (JP)

( * ) Notice: Subject to any disclaimer, the term of this patent is extended or adjusted under 35 U.S.C. 154(b) by 431 days.

(21) Appl. No.: 17/429,830

(22) PCT Filed: Feb. 12, 2020

(86) PCT No.: PCT/JP2020/005397
§ 371 (c)(1),
(2) Date: Aug. 10, 2021

(87) PCT Pub. No.: WO2020/166622
PCT Pub. Date: Aug. 20, 2020

(65) Prior Publication Data
US 2022/0125441 A1  Apr. 28, 2022

(30) Foreign Application Priority Data
Feb. 14, 2019  (JP) ................. 2019-024162

(51) Int. Cl.
A61B 17/15 (2006.01)
A61B 17/00 (2006.01)
A61F 2/46 (2006.01)
(52) U.S. Cl.
CPC .. A61B 17/157 (2013.01); A61B 2017/00991 (2013.01); A61F 2/461 (2013.01)

(58) Field of Classification Search
CPC ................ A61B 17/157; A61B 2017/00991
See application file for complete search history.

(56) References Cited

U.S. PATENT DOCUMENTS

| 5,788,700 A | 8/1998 | Morawa et al. |
| 2005/0070910 A1* | 3/2005 | Keene ................ A61B 17/157 606/88 |
| 2014/0200618 A1 | 7/2014 | Donner et al. |
| 2016/0074151 A1* | 3/2016 | Pfeiffer ................ A61F 2/0805 623/13.17 |

FOREIGN PATENT DOCUMENTS

| JP | 2016-140487 A | 8/2016 |
| WO | 03/013371 A1 | 2/2003 |
| WO | 2015/048319 A1 | 4/2015 |

* cited by examiner

Primary Examiner — Sameh R Boles
(74) Attorney, Agent, or Firm — Procopio, Cory, Hargreaves & Savitch LLP (57) ABSTRACT A surgical instrument includes a rod unit extending in a first direction along a tibia of a human body, an attachment located at a first end of the rod unit that is attachable to an ankle joint, and a fastener located at a second end of the rod unit that is fasten-able to a proximal end of the tibia. The fastener has a through-hole extending in a second direction that crosses the first direction, and a pin that is arranged in the through-hole and that has a tip which is received in the tibia. The through-hole has an opening larger than a profile of the pin to allow the fastener to move about a portion of contact between the through-hole and the pin when the pin is received in the tibia.

15 Claims, 6 Drawing Sheets

SURGICAL INSTRUMENT

FIELD

The present disclosure relates to a surgical instrument for knee replacement.

BACKGROUND

A known surgical instrument for knee replacement includes a cutting guide that guides a cutting instrument for cutting the proximal end of the tibia.

BRIEF SUMMARY

A surgical instrument according to an aspect of the present disclosure includes a rod unit extending in a first direction along a tibia of a human body, an attachment located at a first end of the rod unit that is attachable to an ankle joint, and a fastener located at a second end of the rod unit that is fasten-able to a proximal end of the tibia. The fastener has a through-hole extending in a second direction that crosses the first direction, and a pin that is arranged in the through-hole and that has a tip which is received in the tibia. The through-hole has an opening larger than a profile of the pin to allow the fastener to move about a portion of contact between the through-hole and the pin when the pin is received in the tibia.

A surgical instrument according to another aspect of the present disclosure includes a rod unit extending in a first direction to be along a tibia of a human body, an attachment located at a first end of the rod unit that is attachable to an ankle joint, and a fastener located at a second end of the rod unit that is fasten-able to a proximal end of the tibia. The fastener has a through-hole extending in a second direction that crosses the first direction, and the through hole accommodating a pin having a tip to be received in the tibia. The through-hole has an opening larger than a profile of the pin to allow the fastener to move about a portion of contact between the through-hole and the pin when the pin is received in the tibia. The through-hole has a first opening that is nearer the tibia, and a second opening at an opposite end to the first opening. A diameter of the second opening is larger than a diameter of the first opening.

BRIEF DESCRIPTION OF DRAWINGS

The objects, features, and advantages of the present disclosure will become more apparent from the following detailed description and the drawings.

DETAILED DESCRIPTION

One or more embodiments of the present disclosure will now be described with reference to the drawings. The present disclosure is widely applicable to a surgical instrument for knee replacement.

First, a surgical instrument with a structure that forms the basis of a surgical instrument according to one or more embodiments of the present disclosure will be described.

The surgical instrument with the structure that forms the basis of the surgical instrument according to one or more embodiments of the present disclosure is used in knee replacement in which the proximal end of the tibia and the distal end of the femur are cut and then an artificial knee or implants are attached to the cut portions. The surgical instrument including a cutting guide for guiding a cutting instrument is used in cutting the proximal end of the tibia.

For example, a known surgical instrument for knee replacement is used to position a cutting guide that guides a cutting instrument near the proximal end of the tibia. This surgical instrument includes a lower clamp, a positioning external rod, a tibia positioning shaft, and a cutting guide. The lower clamp is used to attach the surgical instrument to the ankle joint. The positioning external rod is fastened to the femur and extends parallel to the axis of the femur. The tibia positioning shaft includes a base positioner that can hold the positioning external rod. The cutting guide is positioned at an intended cutting position, with the positioning external rod held by the tibia positioning shaft. When the cutting guide is positioned, the surgical instrument is completely fastened to the tibia with the pin.

Knee Replacement and Surgical Instrument Overview

Figure 1:
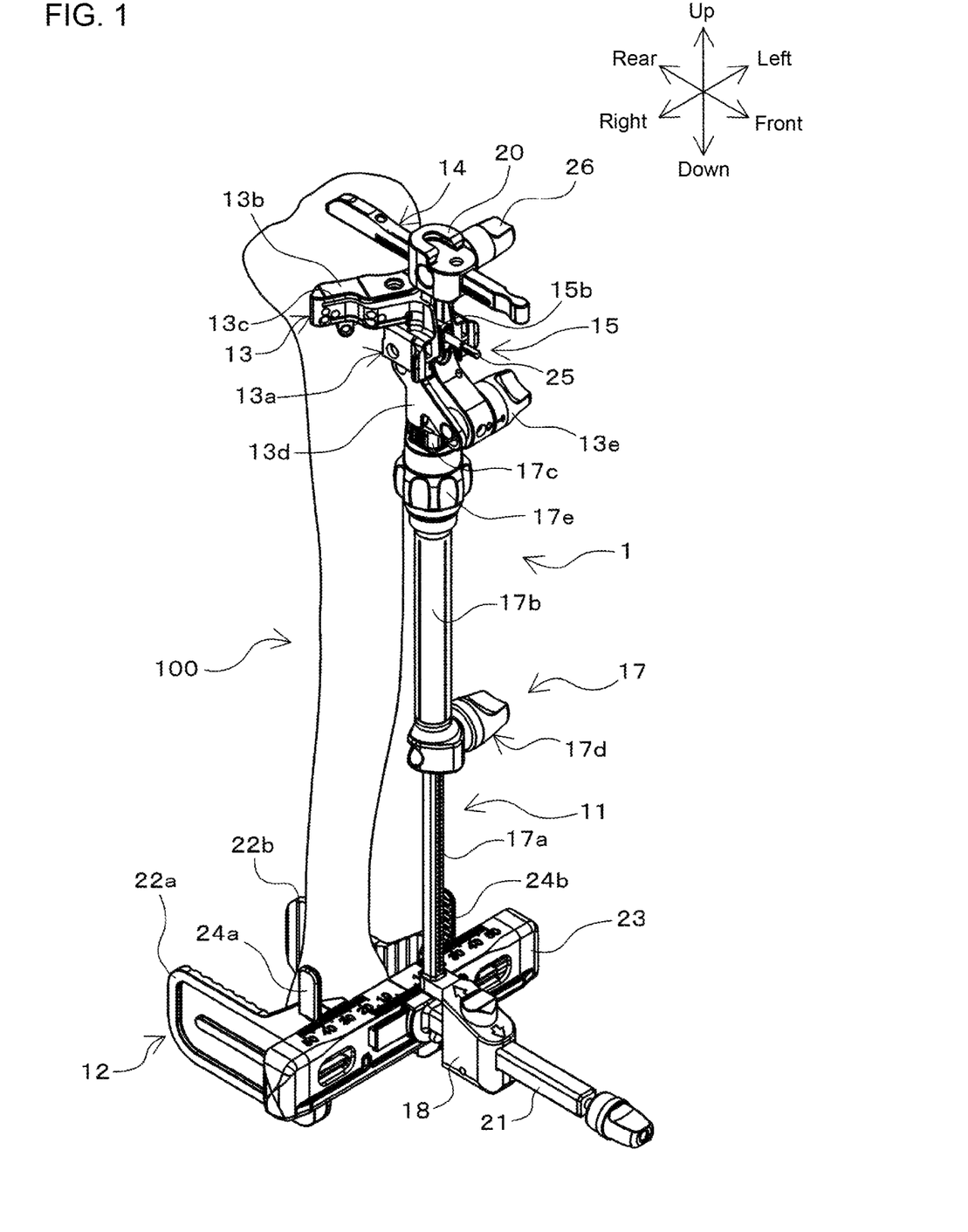
FIG. 1 is a perspective view of a surgical instrument according to one embodiment of the present disclosure.
Figure 2:
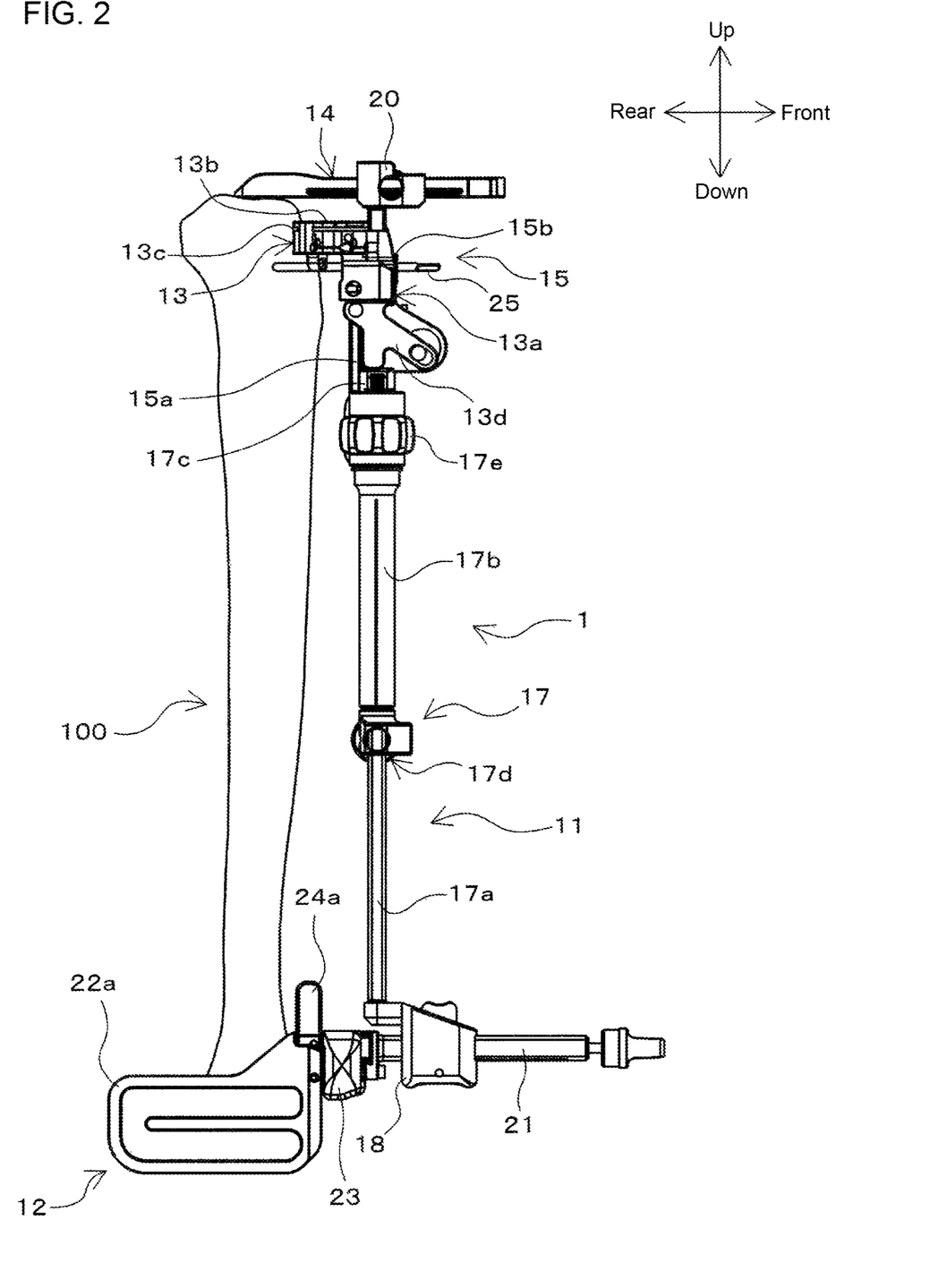
FIG. 2 is a side view of the surgical instrument shown in FIG. 1 with a patient's tibia to schematically show a use example of the surgical instrument.

FIG. 1 is a perspective view of a surgical instrument 1 according to an embodiment of the present disclosure. The surgical instrument 1 is used for knee replacement. Knee replacement is a surgical procedure to replace a malfunctioning knee of a patient with an artificial knee. FIGS. 1 and 2 (described later) schematically show a tibia 100 alone among the regions of the patient body. Other bones or soft tissue in the patient body, such as muscle, are not shown in the figures.

Knee replacement involves cutting of portions at the proximal end of the tibia 100 and the distal end of the femur of the patient, and formation of mount surfaces on which an artificial knee or implants are placed. The artificial knee includes a tibial implant and a femoral implant (both not shown). The tibial implant is placed on the mount surface (not shown) at the proximal end of the tibia 100. The femoral implant is placed on the mount surface (not shown) at the distal end of the femur. Thus, the patient's knee is replaced with the artificial knee. Being proximal herein refers to being closer to the trunk, and being distal herein refers to being farther from the trunk.

As described above, knee replacement involves formation of a mount surface for a tibial implant at the proximal end of the tibia 100. To form the implant mount surface at the proximal end of the tibia 100, the surgical instrument 1 is placed on the tibia 100 to cut part of the proximal end of the tibia 100 with a cutting instrument such as a bone saw (not shown). The surgical instrument 1 including a cutting guide 13 that guides a cutting instrument in a cutting direction is used to cut part of the proximal end of the tibia 100 with the cutting instrument. The surgical instrument 1 will now be described in detail.

FIG. 2 is a side view of the surgical instrument 1 shown in FIG. 1 with the patient's tibia 100 to schematically show a use example of the surgical instrument 1.

Throughout the drawings, the directions pointed with up and down arrows respectively indicate the upper and lower portions of the patient body. The directions pointed with right and left arrows respectively indicate the right and left portions of the patient body. The directions pointed with front and rear arrows respectively indicate the front and rear portions of the patient body. More specifically, the up-down direction, right-left direction, and front-rear direction throughout the drawings indicate the up-down or vertical direction, right-left or lateral direction, and front-rear direction with respect to the patient body.

As shown in FIGS. 1 and 2, the surgical instrument 1 includes a rod unit 11, an attachment 12, a cutting guide 13, a front-rear rod unit 14, and a fastener 15.

Rod Unit

As shown in FIGS. 1 and 2, the rod unit 11 includes a vertical rod 17, a shaft coupler 18, and a front-rear rod support 20.

The vertical rod 17 is placed to extend in a first direction with the surgical instrument 1 placed along the tibia 100. The first direction corresponds to the vertical direction. The first direction also extends along the tibia 100 of the human body. The vertical rod 17 includes a first rod 17a, a second rod 17b, and a third rod 17c. The first rod 17a, the second rod 17b, and the third rod 17c are rod-shaped members linearly extending in, for example, the first direction.

The first rod 17a and the second rod 17b are coaxially coupled in series. The first rod 17a and the second rod 17b have, for example, a substantially polygonal-columnar or cylindrical shape. In the present embodiment, the first rod 17a is, for example, a substantially polygonal-columnar member. The second rod 17b is, for example, a substantially cylindrical member. The first rod 17a is received in the second rod 17b from a lower end or a first end of the second rod 17b. The second rod 17b can change its position in the axial direction relative to the first rod 17a. More specifically, the first rod 17a and the second rod 17b in the vertical rod 17 are extendable and retractable in the axial direction.

In the present embodiment, the first rod 17a is received in the second rod 17b. In some embodiments, the second rod 17b may be received in the first rod 17a.

The vertical rod 17 with the above structure can change its length in the axial direction. More specifically, when placed along the tibia 100, the vertical rod 17 can adjust its length in the first direction. More specifically, the vertical rod 17 can adjust its length by accommodating the first rod 17a in the second rod 17b. The vertical rod 17 includes a first vertical rod lock 17d at a joint portion between the first rod 17a and the second rod 17b. The vertical rod 17 also includes a second vertical rod lock 17e at a joint portion between the second rod 17b and the third rod 17c.

The first vertical rod lock 17d can position the second rod 17b in the axial direction relative to the first rod 17a as intended by a surgeon. The vertical rod 17 can change the position of the second rod 17b relative to the first rod 17a stepwise in response to the surgeon handling the first vertical rod lock 17d.

The third rod 17c extends from the upper end of the second rod 17b in the direction in which the second rod 17b extends. More specifically, the second rod 17b and the third rod 17c are coaxially coupled in series. The third rod 17c is a rod-shaped member with, for example, a substantially rectangular cross-section. The third rod 17c is received in the second rod 17b from the upper end or a second end of the second rod 17b. The third rod 17c can change its position in the axial direction relative to the second rod 17b. More specifically, the third rod 17c can adjust its length by being accommodated in the second rod 17b. The second rod 17b and the third rod 17c in the vertical rod 17 are extendable and retractable in the axial direction.

In the present embodiment, the third rod 17c is received in the second rod 17b. In some embodiments, the second rod 17b may be received in the third rod 17c.

The second vertical rod lock 17e can position the third rod 17c in the axial direction relative to the second rod 17b as intended by a surgeon. The vertical rod 17 can change the position of the third rod 17c relative to the second rod 17b stepwise in response to the surgeon handling the second vertical rod lock 17e.

The shaft coupler 18 couples the vertical rod 17 to the attachment 12. The attachment 12 includes a shaft 21. The shaft coupler 18 can couple the vertical rod 17 to the attachment 12 by coupling the first rod 17a to the shaft 21.

When the surgical instrument 1 is placed along the tibia 100, the shaft 21 extends in a second direction. The second direction is a direction crossing the tibia 100 of the human body, or the front-rear direction of the human body.

The shaft coupler 18 couples the shaft 21 to one end of the first rod 17a, with the axial direction of the shaft 21 orthogonal to the axial direction of the first rod 17a. The shaft coupler 18 couples the shaft 21 to the first rod 17a at the one end of the first rod 17a (or a lower end of the first rod 17a placed in the vertical direction of the human body) opposite to the other end coupled to the second rod 17b.

The shaft coupler 18 has a through-hole in which the shaft 21 is slidable in the axial direction. The surgical instrument 1 can change the position of the vertical rod 17 in the axial direction of the shaft 21 by changing the position of the shaft coupler 18 relative to the shaft 21. The surgical instrument 1 along the tibia 100 can adjust the position of the vertical rod 17 in the second direction relative to the attachment 12.

The shaft coupler 18 also includes a unit for positioning the first rod 17a in the second direction relative to the shaft 21 as intended by a surgeon. For example, the shaft coupler 18 includes an engagement portion that engages the shaft 21 and the first rod 17a with each other under a spring force, and a pressing operation portion that disengages the shaft 21 and the first rod 17a from each other under a spring force. In response to the surgeon handling the pressing operation portion of the shaft coupler 18, the surgical instrument 1 can change the position of the vertical rod 17 in the second direction relative to the attachment 12 stepwise.

The front-rear rod support 20 couples the vertical rod 17 to the front-rear rod unit 14 (described later) to cause the vertical rod 17 to support the front-rear rod unit 14. The front-rear rod support 20 includes, for example, a block with an angular tube shape. The front-rear rod support 20 is located on the upper end of the third rod 17c. More specifically, the front-rear rod support 20 is placed on the third rod 17c with the fastener 15 in between.

The front-rear rod support 20 has a hole receiving the front-rear rod unit 14 slidably in the axial direction. The front-rear rod support 20 holds the front-rear rod unit 14 above the third rod 17c in a manner slidable in the axial direction of the front-rear rod unit 14. When the position of the front-rear rod unit 14 is changed relative to the front-rear rod support 20, the position of the front-rear rod unit 14 is changed relative to the vertical rod 17 in the direction crossing the axial direction of the third rod 17c.

The front-rear rod support 20 includes a unit that adjusts the position of the front-rear rod unit 14 relative to the third rod 17c. For example, the front-rear rod support 20 includes a positioner 26 that is rotatable by the surgeon to position and fix the front-rear rod unit 14 in the front-rear direction.

Attachment

The attachment 12 shown in FIGS. 1 and 2 is a unit attached to the rod unit 11 at a first end of the vertical rod 17 to be fixed to the ankle joint. The attachment 12 includes the shaft 21, a pair of clamps (22a and 22b), and a frame 23.

The shaft 21 extends linearly and includes a columnar portion with a substantially rectangular cross section. When the surgical instrument 1 is placed along the tibia 100, the shaft 21 has the axis in the second direction. As described above, the shaft 21 is coupled to the lower end of the first rod 17a in the vertical rod 17 with the shaft coupler 18. Thus, the attachment 12 is attached to the rod unit 11 at the lower end of the vertical rod 17.

The pair of clamps (22a and 22b) hold the ankle joint between them in the lateral direction to fix the attachment 12 with respect to the ankle joint. The pair of clamps (22a and 22b) are located at the rear of the frame 23. The frame 23 is located behind the lower end of the vertical rod 17 and behind the shaft 21. The frame 23 is a plate extending in a direction perpendicular to the directions in which the vertical rod 17 and the shaft 21 extend. The frame 23 couples the pair of clamps (22a and 22b) and the shaft 21. The shaft 21 has its end attached to the center of the frame 23.

The frame 23 is in front of the ankle joint. The pair of clamps (22a and 22b) are located on the right and left sides of the ankle joint. The frame 23 has, on its upper surface, graduations to measure the dimension by which the pair of clamps (22a and 22b) move.

Each of the clamps (22a and 22b) is cantilevered and slidably attached to the frame 23. The clamps (22a and 22b) include a pair of knobs (24a and 24b) that allow the respective clamps (22a and 22b) to slide relative to the frame 23. Although the soft tissue around the tibia 100 are not shown in the figures, the attachment 12 is fixed to the ankle joint through the soft tissue outside.

Cutting Guide

The cutting guide 13 guides the cutting instrument, such as a bone saw, in the cutting direction when the cutting instrument cuts part of the proximal end of the tibia 100. The cutting guide 13 includes a connector 13a, a slit former 13b, and a guide slot 13c.

The cutting guide 13 is attached to the upper end of the vertical rod 17 (third rod 17c). The cutting guide 13 attached to the vertical rod 17 is cantilevered to extend to the medial side (rightward in FIG. 1) from the rear of the vertical rod 17 when the surgical instrument 1 is placed along the tibia 100.

The connector 13a connects the cutting guide 13 to the vertical rod 17. The connector 13a includes a movable piece 13d, which slidably rotates relative to the third rod 17c, and a movable-piece operation portion 13e, which can slidably operate the movable piece 13d. The connector 13a is rotatable relative to the rod unit 11 to adjust the angle of the cutting guide 13 (or the cutting instrument) to the tibia 100 using the movable piece 13d and the movable-piece operation portion 13e. Thus, the cutting guide 13 connected to the third rod 17c with the connector 13a is rotatable by the surgeon rotating the movable-piece operation portion 13e.

The slit former 13b is a plate that gradually curves and extends from the connector 13a. The slit former 13b gradually curves and extends in conformance with the periphery of the tibia 100 from the front of the tibia 100 to the right or the left.

The slit former 13b has a slit or a guide slot 13c extending through to guide the cutting instrument in the cutting direction when the cutting instrument cuts part of the proximal end of the tibia 100. Upon completion of the position adjustment of the surgical instrument 1 to the tibia 100, the cutting instrument is received in and along the guide slot 13c to cut part of the proximal end of the tibia 100. The cut part of the proximal end of the tibia 100 serves as the mount surface for the tibial implant on the tibia 100.

Front-Rear Rod Unit

With reference to FIGS. 1 and 2, the front-rear rod unit 14 extends linearly and includes, for example, a square-bar portion with a substantially rectangular cross section. The front-rear rod unit 14 is attached to the front-rear rod support 20 and is received in the hole in the front-rear rod support 20. Thus, the front-rear rod unit 14 is attached to the rod unit 11 at the upper end of the vertical rod 17 with the fastener 15.

The front-rear rod unit 14 is supported by the front-rear rod support 20 and is received in the hole in the front-rear rod support 20. Thus, the front-rear rod unit 14 is attached to the rod unit 11, with, for example, the axial direction orthogonal to the axial direction of the third rod 17c. Thus, the front-rear rod unit 14 has its axial direction extending in the second direction when the surgical instrument 1 is placed along the tibia 100. The front-rear rod unit 14 may be fastened to the proximal end of the tibia 100 with a pin (not shown).

Fastener

Figure 3:
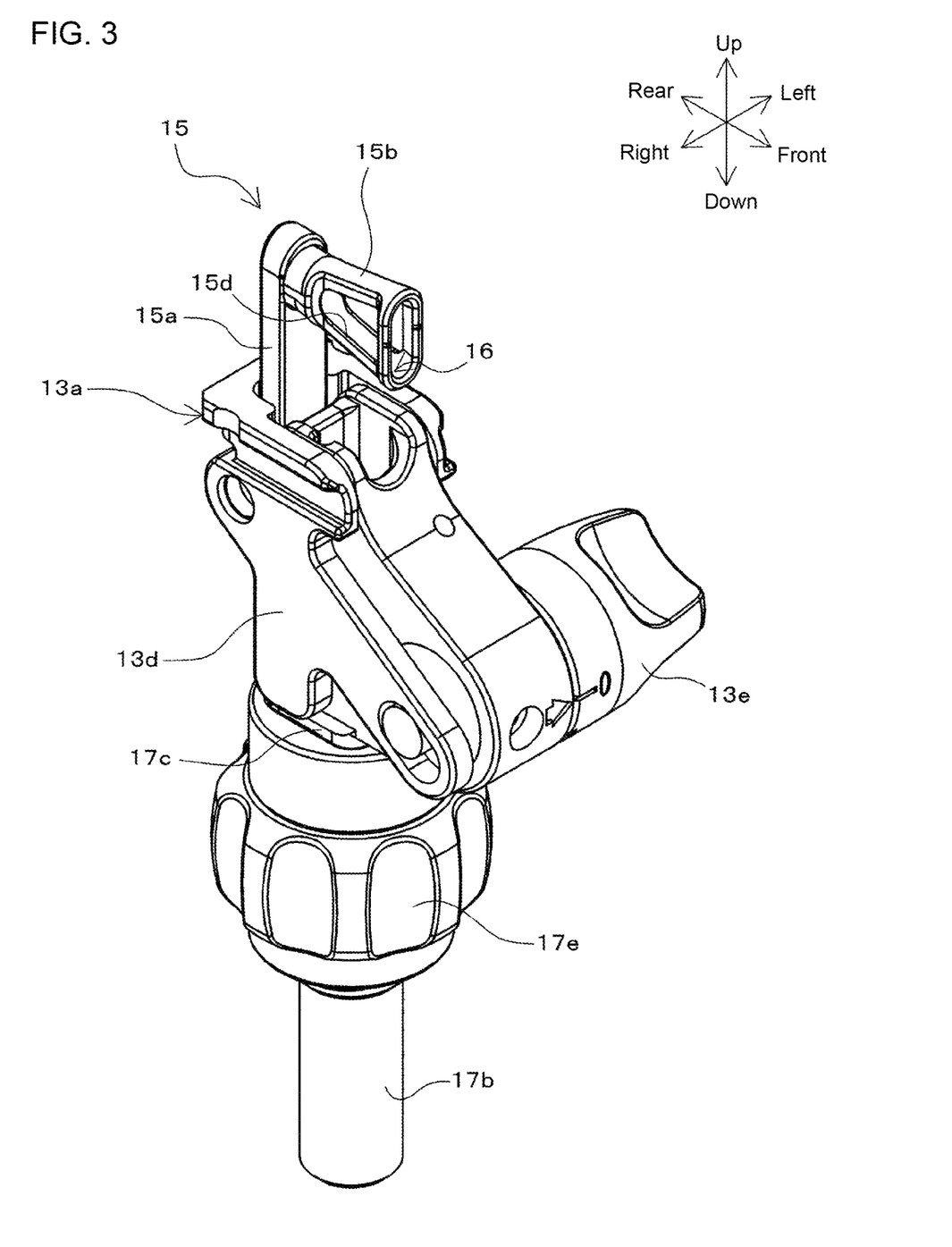
FIG. 3 is a partially enlarged perspective view of the surgical instrument shown in FIG. 1.
Figure 4:
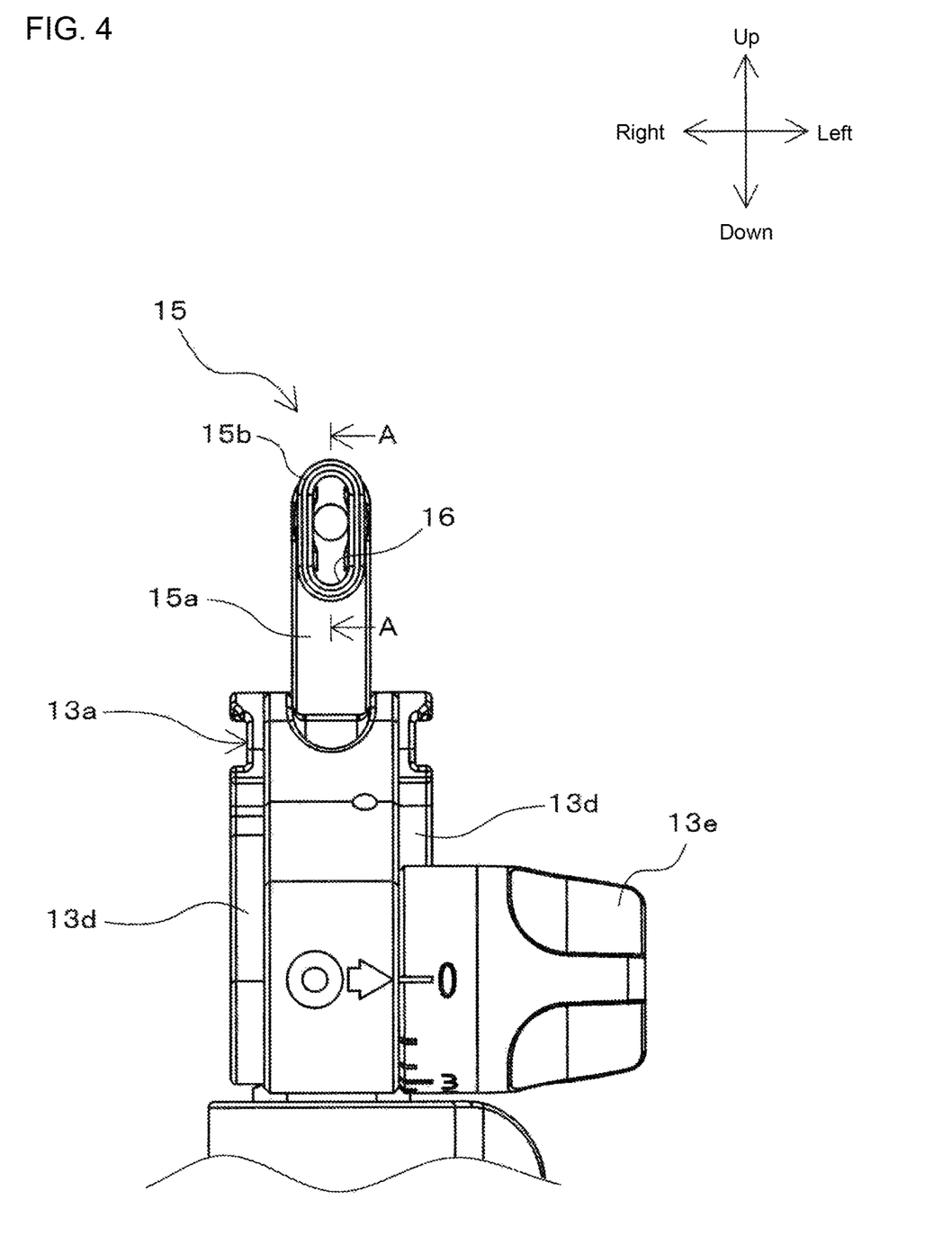
FIG. 4 is a partially enlarged front view of the surgical instrument shown in FIG. 1.
Figure 5:
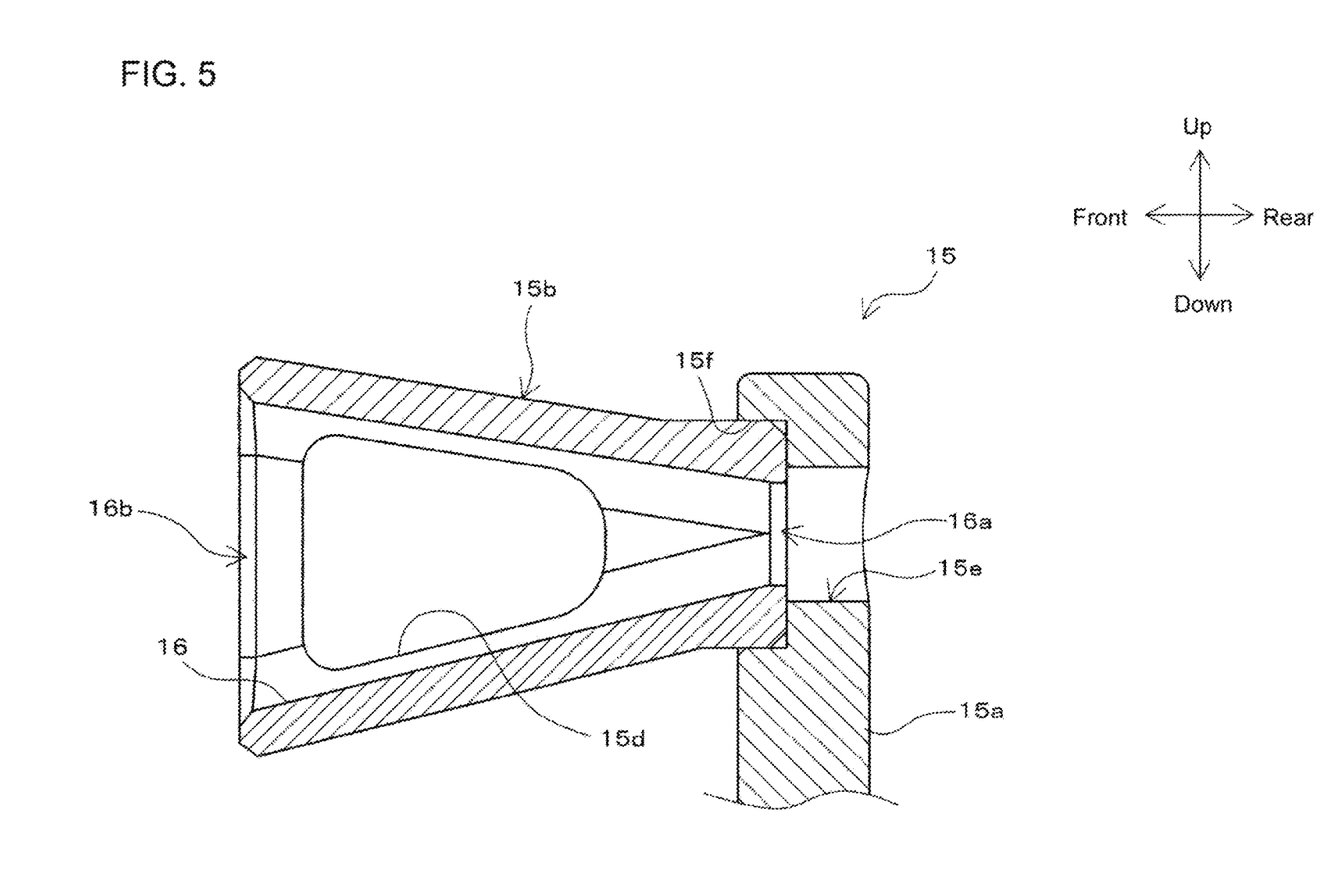
FIG. 5 is a cross-sectional view of the surgical instrument taken along line A-A as viewed in the direction indicated by arrows in FIG. 4.
Figure 6A:
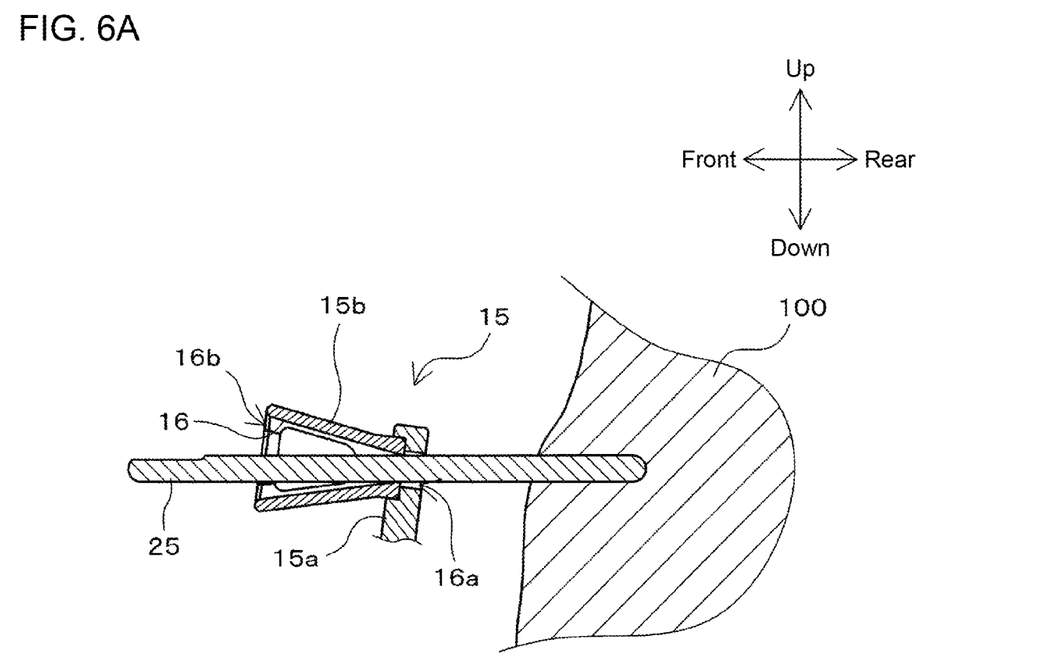
FIG. 6A is a partially enlarged cross-sectional view of the surgical instrument shown in FIG. 1 when the surgical instrument is swung relative to a pin fastened to the tibia.
Figure 6B:
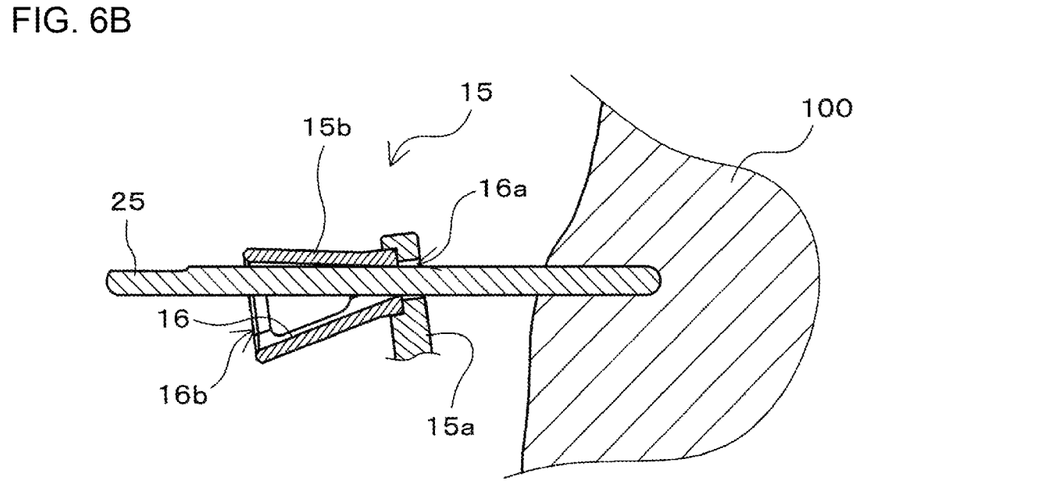
FIG. 6B is a partially enlarged cross-sectional view of the surgical instrument shown in FIG. 1 when the surgical instrument is swung relative to a pin fastened to the tibia.

FIG. 3 is a partially enlarged perspective view of the surgical instrument 1 shown in FIG. 1. FIG. 4 is a partially enlarged front view of the surgical instrument 1 shown in FIG. 1. FIGS. 3 and 4 show the surgical instrument 1 excluding part of the cutting guide 13 and the front-rear rod unit 14, and show part of the cutting guide 13 and the fastener 15 located at a second end of the rod unit 11. FIG. 5 is a cross-sectional view of the surgical instrument 1 taken along line A-A as viewed in the direction indicated by arrows in FIG. 4. FIGS. 6A and 6B are partially enlarged cross-sectional views of the surgical instrument 1 shown in FIG. 1 when the surgical instrument 1 is swung relative to a pin 25 fastened to the tibia 100.

The fastener 15 in the present embodiment is located at the upper end of the rod unit 11. More specifically, the fastener 15 is located on the third rod 17c and a rod connector 15a adjacent to and parallel to the third rod 17c. The fastener 15 is fastened to the proximal end of the tibia 100 with the pin 25 on the front of the tibia 100.

The fastener 15 includes a movement restrictor 15b having a through-hole 16 and the pin 25. The through-hole 16 in the movement restrictor 15b extends in the second direction crossing the first direction and substantially parallel to the front-rear direction of the tibia. The pin 25 is placed in the through-hole 16, with the tip received in the tibia 100. More specifically, the pin 25 is placed in the through-hole 16 from the front to the rear to be received in the proximal end of the tibia 100. The pin 25 is not shown in FIGS. 3 to 5.

The movement restrictor 15b restricts the swinging direction of the surgical instrument 1 relative to the tibia 100 when the surgical instrument 1 is held to be swingable relative to the tibia 100 with the pin 25 placed in the through-hole 16.

The through-hole 16 has a first opening 16a near the tibia 100, and a second opening 16b at an opposite end. The second opening 16b has a larger diameter than the first opening 16a. More specifically, the through-hole 16 has a cross-sectional area increasing from the first opening 16a toward the second opening 16b. The cross-sectional area of the through-hole 16 taken in the first direction continuously increases from the rear toward the front.

The opening of the through-hole 16 is larger than the profile of the pin to allow the fastener 15 to move about a portion of contact between the through-hole 16 and the pin 25 when the pin 25 is received in the tibia 100. More specifically, a portion of the pin 25 in contact with the through-hole 16 is a portion on the outer periphery received in the through-hole 16 and near the first opening 16a of the through-hole 16. A portion of the through-hole 16 in contact with the pin 25 is the inner periphery at the edge of the first opening 16a. As shown in FIGS. 6A and 6B, a clearance left between the fastener 15 and the pin 25 allows the surgical instrument 1 to be held swingable relative to the tibia 100 about a portion of contact between the through-hole 16 and the pin 25.

A surgical instrument with the structure that forms the basis of the surgical instrument according to one or more embodiments of the present disclosure has, for example, a through-hole supporting a pin with substantially the same size as the profile of the pin. This structure causes difficulties in finely adjusting the position of the surgical instrument after the surgical instrument is fastened. In contrast, the surgical instrument 1 according to one or more embodiments of the present disclosure with the above structure enables fine adjustment of the position of the surgical instrument 1 with the operation on the shaft coupler 18 after the surgical instrument 1 is fastened to the tibia 100 as well.

The movement restrictor 15b has an oval cross section taken perpendicular to the second direction. The through-hole 16 in the movement restrictor 15b has a cross-sectional area continuously increasing in the first direction from the rear toward the front. The movement restrictor 15b has windows 15d in its wall surface to enable visual identification of the received pin 25.

The first opening 16a has a shape in conformance with the profile of the pin 25. More specifically, the first opening 16a and the profile of the pin 25 have the same or similar shapes. The profile of the first opening 16a in the present embodiment conforms to the profile of the pin 25 with a cylindrical shape. More specifically, the profile of the first opening 16a has a circular cross section taken perpendicular to the second direction.

The second opening 16b has, for example, an oval shape with the major axis extending in the first direction. More specifically, the second opening 16b has an elliptical shape.

With reference to FIG. 5, the rod connector 15a receives the movement restrictor 15b on the front, or opposite to the tibia 100. The rod connector 15a has a communicating hole 15e extending in the second direction and communicating with the through-hole 16 in the movement restrictor. The movement restrictor 15b is fitted and attached to a setback 15f on the front of the rod connector 15a. The setback 15f is coaxial with the communicating hole 15e and has a larger diameter than the communicating hole 15e. More specifically, the outer periphery of the movement restrictor 15b at the first opening has the same shape as the profile of the inner periphery of the setback 15f to be fitted into and fixed to the setback 15f.

Use Example of Surgical Instrument

The surgical instrument 1 is used for knee replacement in, for example, the procedure described below.

First, the angle of the cutting guide 13 is fixed. More specifically, the connector 13a is rotated with the movable-piece operation portion 13e to set and fix the angle of the cutting guide 13 to achieve the angle of a cut plane of the tibia 100 determined before surgery.

Subsequently, the attachment 12 is fixed to the patient's ankle joint. More specifically, the surgeon handles the pair of clamps (22a and 22b) to fix the attachment 12 to the patient's ankle joint.

When the attachment 12 is fixed to the ankle joint, the surgeon adjusts the position of the vertical rod 17 to arrange the vertical rod 17 substantially parallel to the bone axis of the patient's tibia 100 when viewed from the front. The position of the shaft 21 relative to the attachment 12 is adjusted, and the length of the vertical rod 17 is adjusted by the first vertical rod lock 17d. Thus, the position of the vertical rod 17 in the lateral direction relative to the tibia 100 is adjusted.

Once the position of the vertical rod 17 in the lateral direction relative to the tibia 100 is adjusted, the pin 25 is placed into the through-hole 16 in the fastener 15 to fasten the fastener 15 to the proximal end of the tibia 100. As described above, the through-hole 16 has a cross-sectional area continuously increasing from the first opening 16a toward the second opening 16b. Thus, the surgical instrument 1 is held swingable about the portion of contact between the through-hole and the pin 25. The second opening 16b of the through-hole 16 has an oval shape with the major axis extending in the first direction. Thus, the cutting guide 13 is restricted from moving in the lateral direction but can move in the front-rear direction along the shaft 21.

After the fastener 15 is fastened to the proximal end of the tibia 100, the position of the shaft coupler 18 in the front-rear direction is adjusted to arrange the vertical rod 17 substantially parallel to the bone axis of the patient's tibia 100 when viewed from laterally. Thus, the position of the vertical rod 17 is adjusted. The length of the vertical rod 17 is also adjusted.

The above procedure adjusts the position of the vertical rod 17 in the front-rear and lateral directions relative to the bone axis, and the position of the cutting guide 13 relative to the tibia 100 to an appropriate position. The proximal end of the tibia 100 is then cut by the cutting instrument such as a bone saw. In the present embodiment, the surgical instrument 1 can be finely adjusted in the second direction after being fastened with the pin 25 as well. This structure facilitates position adjustment of the cutting guide 13 for cutting the proximal end of the tibia 100 in knee replacement. After the surgical instrument 1 is fastened with the pin 25 as well, adjusting the length of the third rod 17c with the second vertical rod lock 17e enables fine adjustment of the length of the surgical instrument 1 in the first direction.

Operational Effects of Present Embodiment

The surgical instrument 1 according to the present embodiment includes the rod unit 11 extending in the first direction or a direction to be along the tibia 100 of the human body, the attachment 12 to be attached to the ankle joint, and the fastener 15 to be fastened to the proximal end of the tibia 100. The fastener 15 has the through-hole 16, which can receive the pin 25, and the through-hole 16 has an opening larger than the profile of the pin 25. Thus, the fastener 15 is movable relative to the pin 25 fastened to the proximal end of the tibia 100 about a portion of contact between the through-hole 16 and the pin 25. Thus, after the pin 25 is fastened to the proximal end of the tibia as well, the surgical instrument 1 is held movable and swingable relative to the tibia 100. Thus, the position and orientation of the surgical instrument 1 relative to the tibia 100 can be adjusted by moving the surgical instrument 1.

The surgical instrument 1 thus further facilitates position adjustment relative to the bone.

In the surgical instrument 1, the through-hole 16 has the first opening 16a nearer the tibia, and the second opening 16b at the opposite end. The second opening 16b has a larger diameter than the first opening 16a. Thus, the surgical instrument 1 can move a larger distance at the second opening with a larger opening area than at the first opening 16a, with the pin 25 received in the through-hole 16. More specifically, the surgical instrument 1 is swingable relative to the pin 25. Thus, the surgeon can adjust the position of the surgical instrument 1 while swinging the surgical instrument 1 relative to the pin 25.

In the surgical instrument 1, the second opening 16b has a larger dimension in the first direction and has an oval shape. Thus, the surgeon can swing or move the surgical instrument 1 in the first direction relative to the pin 25 received in the through-hole 16, while restricting the surgical instrument 1 from moving in directions other than the first direction.

In the surgical instrument 1, the first opening 16a has a shape in conformance with the profile of the pin 25. Thus, the range within which the surgical instrument 1 is movable relative to the pin 25 decreases toward the first opening 16a. This structure enables swinging of the surgical instrument 1 relative to the pin 25 but restricts the surgical instrument 1 from sliding in the vertical and lateral directions.

In the surgical instrument 1, the through-hole 16 continuously becomes larger from the first opening 16a toward the second opening 16b. The through-hole 16 has no protrusion inside. This structure does not largely restrict movement of the surgical instrument 1 also when the surgical instrument 1 is swung.

The surgical instrument 1 according to the present embodiment includes the rod unit 11 extending in the first direction or the direction to be along the tibia 100 of the human body, the attachment 12 to be attached to the ankle joint, and the fastener 15 to be fastened to the proximal end of the tibia 100. The fastener 15 has the through-hole 16, which can receive the pin 25, and the through-hole 16 has an opening larger than the profile of the pin 25. Thus, the fastener 15 is movable relative to the pin 25 fastened to the proximal end of the tibia 100 about a portion of contact between the through-hole 16 and the pin 25. Thus, after the pin 25 is fastened to the proximal end of the tibia as well, the position and the orientation of the surgical instrument 1 relative to the tibia 100 can be adjusted by moving the surgical instrument 1.

Thus, the surgical instrument 1 facilitates position adjustment to the bone.

In the surgical instrument 1, the through-hole 16 has the first opening 16a nearer the tibia, and the second opening 16b at the opposite end. The second opening 16b has a larger opening area than the first opening 16a. Thus, the surgical instrument 1 can move a larger distance at the second opening 16b with a larger opening area than at the first opening 16a, with the pin 25 received in the through-hole 16. More specifically, the surgical instrument 1 is swingable relative to the pin 25. Thus, the surgeon can adjust the position of the surgical instrument 1 while swinging the surgical instrument 1 relative to the pin 25.

Modifications

Although an embodiment of the present disclosure has been described above, the present disclosure is not limited to the above embodiment and may be changed in various manners within the scope of claims. For example, the present disclosure may be modified in the following forms.

(1) The structure according to the above embodiment includes the pin 25 and the movement restrictor 15b with the through-hole 16, but the structure is not limited to the above example. More specifically, for example, the fastener 15 includes the pin 25 as its component. In one modification, for example, the fastener 15 may include the movement restrictor 15b with the through-hole 16. More specifically, the surgical instrument in this modification includes the rod unit 11, the attachment 12, and the fastener 15. The rod unit 11 extends linearly in the first direction to be along the tibia 100 of the human body. The attachment 12 is located at a first end of the rod unit 11 to be attached to the ankle joint.

The fastener 15 is located at a second end of the rod unit 11 to be fastened to the proximal end of the tibia 100. The second end is the upper end when the vertical rod 17 is placed in the vertical direction of the human body. The fastener 15 has the through-hole 16 extending in the second direction crossing the first direction. The fastener 15 can receive the pin 25 having the tip to be received in the tibia 100.

The through-hole 16 has an opening larger than the profile of the pin 25 to allow the fastener 15 to move about a portion of contact between the through-hole 16 and the pin 25 when the pin 25 is received in the tibia 100. The through-hole 16 has the first opening 16a to be nearer the tibia 100, and the second opening 16b at the opposite end to the first opening 16a. The second opening 16b has a larger diameter than the first opening 16a.

The surgical instrument according to the present modification includes the rod unit 11 extending in the first direction or a direction to be along the tibia 100 of the human body, the attachment 12 located at the first end of the rod unit 11 to be attached to the ankle joint, and the fastener 15 located at the second end of the rod unit 11 to be fastened to the proximal end of the tibia 100. The fastener 15 has the through-hole 16, which can receive the pin 25, and the through-hole 16 has the opening larger than the profile of the pin 25. In this structure, a clearance left between the fastener 15 and the pin 25 allows the fastener 15 to move relative to the pin 25 fastened to the proximal end of the tibia 100 about a portion of contact between the through-hole 16 and the pin 25. Thus, after the pin 25 is fastened to the proximal end of the tibia as well, the surgical instrument is held movable and swingable relative to the tibia 100 to adjust its orientation and position in the first direction.

The surgical instrument with the above structure can thus further facilitate position adjustment relative to a bone.

In the surgical instrument according to the present modification, the through-hole 16 has the first opening 16a nearer the tibia 100, and the second opening 16b at the opposite end to the first opening 16a. The second opening 16b has a larger opening area than the first opening 16a. Thus, the surgical instrument can move a larger distance at the second opening 16b with a larger opening area than at the first opening 16a, with the pin 25 received in the through-hole 16. More specifically, the surgical instrument is swingable relative to the pin 25. Thus, the surgeon can adjust the position of the surgical instrument while swinging the surgical instrument relative to the pin 25.

(2) In the above embodiment, for example, the through-hole 16 in the movement restrictor 15b has a cross-sectional area continuously increasing in the first direction from the rear toward the front. However, this example is not limitative. For example, the movement restrictor 15b may have a hollow cylindrical shape, and the through-hole 16 in the movement restrictor 15b may have a uniform opening dimension in the front-rear direction.

(3) In the above embodiment, for example, the movement restrictor 15b has an oval cross section taken perpendicular to the second direction. However, this example is not limitative. For example, the movement restrictor 15b may have a rectangular cross section taken perpendicular to the second direction.

The embodiments may be implemented in the forms described below.

A surgical instrument according to one or more embodiments of the present disclosure includes a rod unit extending in a first direction to be along a tibia of a human body, an attachment located at a first end of the rod unit to be attached to an ankle joint, and a fastener located at a second end of the rod unit to be fastened to a proximal end of the tibia. The fastener has a through-hole extending in a second direction crossing the first direction, and a pin placeable in the through-hole and having a tip to be received in the tibia. The through-hole has an opening larger than a profile of the pin to allow the fastener to move about a portion of contact between the through-hole and the pin when the pin is received in the tibia.

In the above structure, the surgical instrument includes a rod unit extending in a first direction to be along a tibia of a human body, an attachment to be attached to an ankle joint, and a fastener to be fastened to a proximal end of the tibia. The fastener has a through-hole that can receive a pin, and the through-hole has an opening larger than a profile of the pin. The fastener is thus movable relative to the pin fastened to the proximal end of the tibia about a portion of contact between the through-hole and the pin. After the pin is fastened to the proximal end of the tibia as well, the surgical instrument is held movable and swingable relative to the tibia and can adjust its position and orientation relative to the tibia.

The surgical instrument with the above structure can further facilitate position adjustment relative to a bone.

The through-hole may have a first opening to be nearer the tibia, and a second opening at an opposite end to the first opening, and the second opening may have a larger diameter than the first opening.

In this structure, the through-hole has a first opening nearer the tibia, and a second opening at the opposite end. The second opening has a larger diameter than the first opening. Thus, with the pin received in the through-hole, the surgical instrument can move a larger distance at the second opening with a larger opening area than at the first opening. More specifically, the surgical instrument is swingable relative to the pin. Thus, the surgeon can adjust the position of the surgical instrument while swinging the surgical instrument relative to the pin.

The second opening may have an oval shape with the major axis extending in the first direction.

In this structure, the second opening has a larger dimension in the first direction. The second opening has an oval shape. Thus, the surgeon can move and swing the surgical instrument in the first direction relative to the pin received in the through-hole while restricting the surgical instrument from moving in directions other than the first direction.

The first opening may have a shape in conformance with the profile of the pin.

In this structure, the first opening has a shape in conformance with the profile of the pin. Thus, the range within which the surgical instrument is movable relative to the pin decreases toward the first opening. Thus, the surgical instrument is swingable relative to the pin but is restricted from sliding in the vertical and lateral directions.

The through-hole may have a cross-sectional area continuously increasing from the first opening toward the second opening.

In this structure, the through-hole continuously becomes larger from the first opening toward the second opening. Thus, the through-hole has no protrusion inside. This structure does not largely restrict movement of the surgical instrument also when the surgical instrument is swung.

The second direction may extend in a front-rear direction of the tibia.

In this structure, after the pin is fastened to the tibia as well, the surgical instrument can move in a front-rear direction of the tibia.

The surgical instrument may include a cutting guide to guide a cutting instrument to cut the tibia.

This structure can facilitate adjustment of the angle and the cut position of the tibia.

The surgical instrument may include a front-rear rod unit slidable relative to the fastener in the second direction.

In this structure, the front-rear rod unit can be used to check the position of the proximal end of the tibia, and accurately determine the cut position.

A surgical instrument according to one or more embodiments of the present disclosure includes a rod unit extending in a first direction to be along a tibia of human body, an attachment located at a first end of the rod unit to be attached to an ankle joint, and a fastener located at a second end of the rod unit to be fastened to a proximal end of the tibia. The fastener has a through-hole extending in a second direction crossing the first direction, and receiving a pin having a tip to be received in the tibia. The through-hole has an opening larger than a profile of the pin to allow the fastener to move about a portion of contact between the through-hole and the pin when the pin is received in the tibia. The through-hole has a first opening to be nearer the tibia, and a second opening at an opposite end to the first opening. The second opening has a larger diameter than the first opening.

In the above structure, the surgical instrument includes a rod unit extending in a first direction to be along a tibia of a human body, an attachment to be attached to an ankle joint, and a fastener to be fastened to a proximal end of the tibia. The fastener has a through-hole that can receive a pin, and the through-hole has an opening larger than a profile of the pin. The fastener is thus movable about a portion of contact between the through-hole and the pin relative to the pin fastened to the proximal end of the tibia. After the pin is fastened to the proximal end of the tibia as well, the surgical instrument is movable and can adjust its position and orientation relative to the tibia.

The surgical instrument with the above structure can thus further facilitate position adjustment relative to the bone.

In this structure, the through-hole has a first opening nearer the tibia, and a second opening at the opposite end to the first opening. The second opening has a larger opening area than the first opening. Thus, with the pin received in the through-hole, the surgical instrument can move a larger distance at the second opening with a larger opening area than at the first opening. More specifically, the surgical instrument is swingable relative to the pin. Thus, the surgeon can adjust the position of the surgical instrument while swinging the surgical instrument relative to the pin.

The surgical instrument according to one or more embodiments of the present disclosure can facilitate position adjustment.

INDUSTRIAL APPLICABILITY

The present disclosure is widely applicable to a surgical instrument for knee replacement.

REFERENCE SIGNS LIST 1 surgical instrument
11 rod unit
12 attachment
15 fastener
16 through-hole
16a first opening
16b second opening
100 tibia
25 pin

The invention claimed is:

1. A surgical instrument, comprising: a rod unit configured to extending in a first direction along a tibia of a human body; an attachment located at a first end of the rod unit that is attachable to an ankle joint; and a fastener located at a second end of the rod unit that is fastenable to a proximal end of the tibia, the fastener comprising: a rod connector comprising a communicating hole and a setback, a movement restrictor having a first end nearer the tibia, the first end configured to fit into the setback and attach to the rod connector, a through-hole extending through the movement restrictor in a second direction that crosses the first direction, the through-hole comprising a first opening that is nearer the tibia, and a second opening at an opposite end to the first opening, the communicating hole having a diameter that is larger than a diameter of the first opening, and a pin that is configured to be arranged in the through-hole and the communicating hole and that has a tip which is configured to be received in the tibia, wherein the through-hole has an opening larger than a profile of the pin to allow the fastener to move about a portion of contact between the through-hole and the pin when the pin is received in the tibia.

2. The surgical instrument according to claim 1, wherein the through-hole has a first opening that is nearer the tibia, and a second opening at an opposite end to the first opening, and
a diameter of the second opening is larger than a diameter of the first opening.

3. The surgical instrument according to claim 2, wherein the second opening has an oval shape with a major axis extending in the first direction.

4. The surgical instrument according to claim 2, wherein the first opening has a shape in conformance with the profile of the pin.

5. The surgical instrument according to claim 4, wherein the through-hole has a cross-sectional area continuously increasing from the first opening toward the second opening.

6. The surgical instrument according to claim 1, wherein the second direction extends in a front-rear direction of the tibia.

7. The surgical instrument according to claim 1, further comprising: a cutting guide located at the second end of the rod unit, the cutting guide configured to guide a cutting instrument to cut the tibia.

8. The surgical instrument according to claim 1, further comprising: a front-rear rod unit slidable relative to the fastener in the second direction.

9. The surgical instrument according to claim 1, further comprising at least one window in a wall surface of the movement restrictor, the at least one window configured to provide visual identification of the pin.

10. The surgical instrument according to claim 1, wherein a diameter in a major axis of the second opening is larger than the diameter of the communicating hole and the diameter of the first opening.

11. A surgical instrument, comprising: a rod unit configured to extending in a first direction along a tibia of a human body; an attachment located at a first end of the rod unit that is attachable to an ankle joint; and a fastener located at a second end of the rod unit that is fastenable to a proximal end of the tibia, the fastener comprising: a rod connector comprising a communicating hole and a setback, a movement restrictor having a first end nearer the tibia, the first end configured to fit into the setback and attach to the rod connector, a through-hole extending through the movement restrictor in a second direction that crosses the first direction, the through hole and the communicating hole configured to accommodate a pin having a tip to be received in the tibia; wherein the through-hole has an opening larger than a profile of the pin to allow the fastener to move about a portion of contact between the through-hole and the pin when the pin is received in the tibia, the through-hole has a first opening that is nearer the tibia and in communication with the communicating hole, and a second opening at an opposite end to the first opening, and a diameter of the second opening is larger than a diameter of the first opening and the diameter of the first opening is smaller than a diameter of the communicating hole.

12. The surgical instrument according to claim 11, wherein the second direction extends in a front-rear direction of the tibia.

13. The surgical instrument according to claim 11, further comprising: a cutting guide located at the second end of the rod unit, the cutting guide configured to guide a cutting instrument to cut the tibia.

14. The instrument according to claim 11, further comprising: a front-rear rod unit slidable relative to the fastener in the second direction.

15. The instrument according to claim 11, further comprising at least one window in a wall surface of the movement restrictor, the at least one window configured to provide visual identification of the pin.

* * * * *